United States Patent
Dong et al.

(10) Patent No.: US 9,482,124 B2
(45) Date of Patent: Nov. 1, 2016

(54) METHOD FOR DETECTING ABNORMALLY FREQUENT DIESEL PARTICULATE FILTER REGENERATION, ENGINE AND EXHAUST AFTERTREATMENT SYSTEM, AND WARNING SYSTEM AND METHOD

(75) Inventors: Qunlong Dong, Frederick, MD (US); Jeffrey Marley, Hagerstown, MD (US)

(73) Assignee: Mack Trucks, Inc., Greensboro, NC (US)

( * ) Notice: Subject to any disclaimer, the term of this patent is extended or adjusted under 35 U.S.C. 154(b) by 0 days.

(21) Appl. No.: 14/409,286

(22) PCT Filed: Jun. 21, 2012

(86) PCT No.: PCT/US2012/043524
§ 371 (c)(1),
(2), (4) Date: Dec. 18, 2014

(87) PCT Pub. No.: WO2013/191698
PCT Pub. Date: Dec. 27, 2013

(65) Prior Publication Data
US 2015/0167517 A1     Jun. 18, 2015

(51) Int. Cl.
*F01N 3/023* (2006.01)
*F01N 11/00* (2006.01)
(Continued)

(52) U.S. Cl.
CPC .............. *F01N 3/029* (2013.01); *F01N 3/023* (2013.01); *F01N 3/103* (2013.01); *F01N 9/00* (2013.01);
(Continued)

(58) Field of Classification Search
CPC ........ F01N 3/023; F01N 3/029; F01N 3/103; F01N 9/00; F01N 9/002; F01N 9/005; F01N 11/00; F02D 41/0235; F02D 41/029; F02D 41/1445; F02D 41/1446; F02D 41/1448; F02D 41/1454; F02D 41/146; F02D 41/1467; F02D 2200/0414; F02D 2200/0618; F02D 2200/0812; F02D 2200/101; G01N 33/0037; G01M 15/106; Y02T 10/47
USPC .......... 60/274, 277, 295, 297, 311; 73/23.33
See application file for complete search history.

(56) References Cited

U.S. PATENT DOCUMENTS 6,947,831 B2   9/2005  Van Nieuwstadt
8,011,179 B2   9/2011  Scaife et al.
(Continued)

FOREIGN PATENT DOCUMENTS

EP      1529929 A1      5/2005
EP      1722082 A2     11/2006
(Continued)

OTHER PUBLICATIONS

International Search Report (Sep. 20, 2012) for corresponding International Application PCT/US2012/043524.
(Continued)

*Primary Examiner* — Audrey K Bradley
(74) *Attorney, Agent, or Firm* — WRB-IP LLP

(57) ABSTRACT

A method is provided for detecting abnormally frequent diesel particulate filter (DPF) regeneration. The method includes measuring a pressure drop across the DPF and using the measured pressure drop to calculate a pressure drop based soot load estimate, calculating soot output from an engine model and using the calculated soot output to calculate an emissions based soot load estimate, comparing the pressure drop based soot load estimate with the emissions based soot load estimate, and providing a warning if a difference between the pressure drop based soot load estimate and the emissions based soot load estimate exceeds a predetermined.

15 Claims, 3 Drawing Sheets

(51) Int. Cl.
    *F01N 3/029*     (2006.01)
    *F01N 3/10*     (2006.01)
    *F01N 9/00*     (2006.01)
    *F02D 41/14*     (2006.01)
    *F02D 41/02*     (2006.01)
    *G01M 15/10*     (2006.01)
    *G01N 33/00*     (2006.01)
    *F01N 13/00*     (2010.01)

(52) U.S. Cl.
    CPC ............ *F01N 9/002* (2013.01); *F01N 9/005* (2013.01); *F01N 11/00* (2013.01); *F01N 13/009* (2014.06); *F02D 41/029* (2013.01); *F02D 41/0235* (2013.01); *F02D 41/1448* (2013.01); *F02D 41/1467* (2013.01); *G01M 15/106* (2013.01); *G01N 33/0037* (2013.01); *F01N 2560/08* (2013.01); *F01N 2560/14* (2013.01); *F01N 2900/1606* (2013.01); *F02D 41/146* (2013.01); *F02D 41/1445* (2013.01); *F02D 41/1446* (2013.01); *F02D 41/1454* (2013.01); *F02D 2200/0414* (2013.01); *F02D 2200/0618* (2013.01); *F02D 2200/0812* (2013.01); *F02D 2200/101* (2013.01); *Y02T 10/47* (2013.01)

(56) References Cited

U.S. PATENT DOCUMENTS

| | | | |
|---|---|---|---|
| 8,051,645 | B2 | 11/2011 | Chamarthi et al. |
| 2005/0016137 | A1 | 1/2005 | Hamahata |
| 2009/0139211 | A1 | 6/2009 | Berke et al. |
| 2010/0058743 | A1 | 3/2010 | Tsukada |
| 2011/0000190 | A1 | 1/2011 | Svensson et al. |
| 2011/0120088 | A1* | 5/2011 | George ............ F01N 3/021 60/274 |
| 2012/0023903 | A1 | 2/2012 | Oemke et al. |
| 2012/0023911 | A1 | 2/2012 | Liu |

FOREIGN PATENT DOCUMENTS

| | | | | |
|---|---|---|---|---|
| EP | 2218884 | A1 | 8/2010 | |
| EP | 2436900 | A2 | 4/2012 | |
| GB | 2479122 | A | 10/2011 | |
| JP | 2003083035 | A | 3/2003 | |
| JP | 2005344619 | A | 12/2005 | |
| JP | 2010101205 | A | 5/2010 | |
| JP | 2010156241 | A | 7/2010 | |
| SE | WO 2012030279 | A1 * | 3/2012 | ............ F01N 9/002 |

OTHER PUBLICATIONS

International Preliminary Report on Patentability (Jun. 2, 2014) for corresponding International Application PCT/US2012/043524.
Abstract KR20080000430A (Jan. 2, 2008) Kia Motors Corp. (with original document).
Extended European Search Report dated Mar. 1, 2016 for corresponding European application No. 12879371.8.
1st Office Action dated Mar. 29, 2016 for corresponding Japan application No. 2015-518384 translated.
Chinese Official Action (Aug. 22, 2016) for corresponding Chinese App. 201280074111.6.

* cited by examiner

METHOD FOR DETECTING ABNORMALLY FREQUENT DIESEL PARTICULATE FILTER REGENERATION, ENGINE AND EXHAUST AFTERTREATMENT SYSTEM, AND WARNING SYSTEM AND METHOD

BACKGROUND AND SUMMARY

The present invention relates to engines and exhaust after treatment systems and, more particularly, to methods and apparatus for determining whether diesel particulate filter (DPF) regeneration is too frequent.

Modern diesel engines are ordinarily provided with DPFs to filter particulate matter such as unburned hydrocarbons in the engine exhaust. As soot collects in a DPF, it becomes necessary to remove the soot, ordinarily by a process referred to as regeneration. There are two primary mechanisms employed for regeneration: oxidation of soot by O2 (($C+O_2 \rightarrow CO_2$) and/or ($2C+O_2 \rightarrow 2CO$)) called O2-based regeneration and oxidation of soot by NO2 (($C+2NO_2 \rightarrow CO_2+2NO$) and/or ($C+NO_2 \rightarrow CO+NO$)) called NO2-based regeneration. U.S. patent application Ser. No. 12/864,328, entitled "METHOD AND APPARATUS FOR REGENERATING A CATALYZED DIESEL PARTICULATE FILTER (DPF) VIA ACTIVE NO2-BASED REGENERATION WITH ENHANCED EFFECTIVE NO2 SUPPLY", and U.S. patent application Ser. No. 12/864,330, entitled "METHOD AND APPARATUS FOR NO2-BASED REGENERATION OF DIESEL PARTICULATE FILTERS USING RECIRCULATED NOX" both of which are incorporated by reference, describe using modeling to calculate soot load in a DPF. Regeneration by O2 is typically referred to as "active" regeneration as it ordinarily involves the addition of heat to burn off soot that has collected in the DPF, although some O2 regeneration often occurs during normal operation of the engine and exhaust after treatment system (EATS). Regeneration by NO2 is typically referred to as "passive" regeneration and is the primary mechanism by which the DPF is continuously regenerated during normal operation of the engine and EATS.

Soot accumulation in the DPF is affected by engine-out soot as well as by catalytic activity of EATS components such as diesel oxidation catalysts (DOCs) and DPF catalysts, as well as by factors such as engine exhaust temperature and NOx levels. Under many operating conditions, such as during normal highway operation of a truck having a diesel engine, passive regeneration can prevent substantial soot build-up in a DPF, and may avoid the need for active regeneration altogether. Under less favorable conditions, such as local operation at unfavorable exhaust temperatures, soot builds up in the DPF and an active regeneration must be performed.

One way of determining whether an active regeneration is necessary is by measuring pressure drop across the DPF and estimating soot load as a function of the pressure drop at the particular exhaust temperature and exhaust mass flow rate at which the engine is being operated. If this pressure drop soot load estimate exceeds a predetermined soot load limit, an active regeneration will be initiated.

The inventors have recognized that too frequent regeneration may be indicative of a problem, ordinarily a problem associated with either excessive soot generation by the engine or inadequate catalytic activity by the DOC, although other factors such as inadequate catalytic activity by the DPF or reduced DPF effective volume (such as when the DPF is filled with ash) may also or alternatively be behind frequent regenerations. Failure to identify such problems can lead to catastrophic engine or catalyst failures.

Currently, whether regeneration is occurring too frequently is determined by comparing the frequency of regeneration with a predicted regeneration frequency, i.e., a specific time interval. However, as noted, under certain conditions, a truck may not need any regeneration while, under other conditions, the same truck may need a regeneration every few days. This variation makes it difficult to use a single or particular time interval criteria to define what normal DPF regeneration frequency is because a particular interval may be too frequent for a truck operated primarily on the highway, while being normal or too infrequent for a truck operated in stop-and-go traffic.

It is desirable to provide a method and apparatus the can reliably facilitate detection of whether DPF regeneration is occurring too frequently. It is further desirable to provide such as method and apparatus that involves the use of minimal additional equipment. In addition to reasons relating to avoiding engine or catalyst failures, it is desirable to detect excessive DPF regeneration to comply with regulations such as California Code of Regulations: CCR 1971.1 (e)(8.2.2) *Frequent Regeneration*, Code of Federal Regulations: CFR Part 86.010-18 paragraph (g)(8)(ii)(B) *DPI Regeneration Frequency*.

According to an aspect of the present invention, a method is provided for detecting abnormally frequent diesel particulate filter (DPF) regeneration. The method comprises measuring a pressure drop across the DPF and using the measured pressure drop to calculate a pressure drop based soot load estimate, calculating soot output from an engine model and using the calculated soot output to calculate an emissions based soot load estimate, comparing the pressure drop based soot load estimate with the emissions based soot load estimate, and providing a warning if a difference between the pressure drop based soot load estimate and the emissions based soot load estimate exceeds a predetermined value.

According to another aspect of the present invention, a method is provided for detecting possible diesel engine malfunction or diesel oxidation catalyst (DOC) malfunction. The method comprises measuring a pressure drop across a diesel particulate filter (DPF) and using the measured pressure drop to calculate a pressure drop based soot load estimate, calculating soot output from an engine model and using the calculated soot output to calculate a emissions based soot load estimate, comparing the pressure drop based soot load estimate with the emissions based soot load estimate, and checking functionality of the diesel engine and the DOC malfunction if a difference between the pressure drop based soot load estimate and the emissions based soot load estimate exceeds a predetermined value.

According to another aspect of the present invention, a diesel engine with an exhaust after treatment system is provided and comprises the diesel engine, the diesel engine comprising an exhaust, a diesel oxidation catalyst (DOC) downstream of the diesel engine exhaust, a diesel particulate filter (DPF) downstream of the DOC, sensors for measuring a pressure drop across the DPF, and a controller. The controller is arranged to arranged to calculate a pressure drop based soot load estimate based on the measured pressure drop, calculate an emissions based soot load estimate based on soot output calculated from an engine model, compare the pressure drop based soot load estimate with the emissions based soot load estimate, and provide a warning if a difference between the pressure drop based soot load estimate and the emissions based soot load estimate exceeds a predetermined value.

According to another aspect of the present invention, a warning system for diesel engine with an exhaust after treatment system is provided, the exhaust after treatment system comprising a diesel oxidation catalyst (DOC) downstream of an exhaust of the engine and a diesel particulate filter (DPF) downstream of the DOC. The warning system comprises sensors for measuring a pressure drop across the DPF, and a controller arranged to calculate a pressure drop based soot load estimate based on the measured pressure drop, calculate an emissions based soot load estimate based on soot output calculated from an engine model, compare the pressure drop based soot load estimate with the emissions based soot load estimate, and provide a warning if a difference between the pressure drop based soot load estimate and the emissions based soot load estimate exceeds a predetermined value.

BRIEF DESCRIPTION OF THE DRAWINGS

The features and advantages of the present invention are well understood by reading the following detailed description in conjunction with the drawings in which like numerals indicate similar elements and in which.

DETAILED DESCRIPTION

Figure 1:
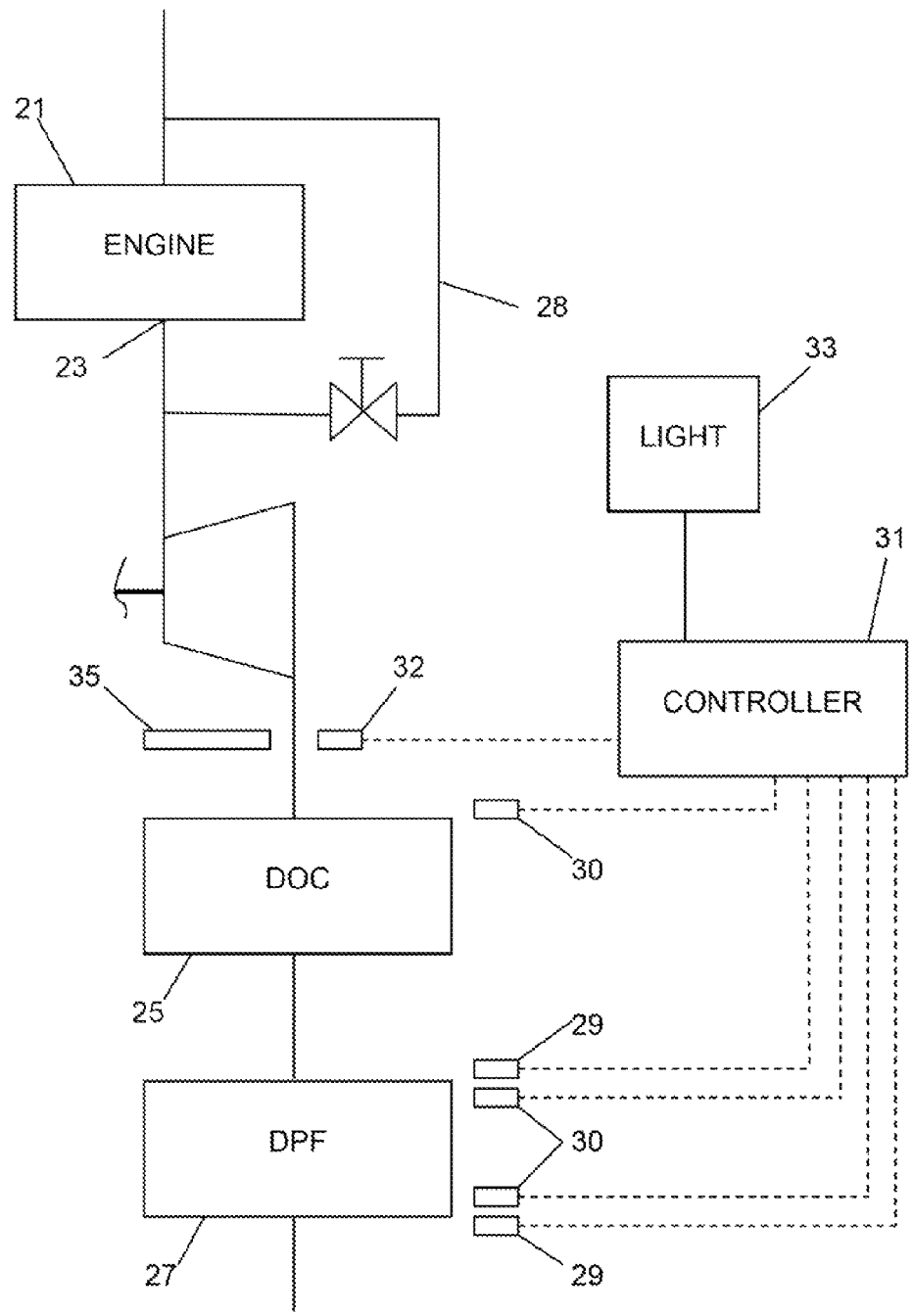
FIG. 1 is a schematic illustration of an engine and an exhaust aftertreatment system according to an aspect of the present invention.

A diesel engine 21 with an exhaust after treatment system (EATS) according to an aspect of the present invention is shown schematically in FIG. 1. The engine 21 comprises an exhaust 23 and the aftertreatment system comprises a diesel oxidation catalyst (DOC) 25 downstream of the diesel engine exhaust, and a diesel particulate filter (DPF) 27 downstream of the DOC. The EATS may comprise an Exhaust Gas Recirculation (EGR) arrangement 28.

Sensors 29 are provided for measuring a pressure drop across the DPF and send a signal to a controller 31. The controller 31 may be any suitable form of controller, such as a conventional CPU, and is arranged to calculate what shall be denominated as a pressure drop based soot load estimate SLp based on the measured pressure drop ($\Delta P$). The pressure drop based soot load estimate SLp is ordinarily based on additional factors including measured exhaust mass flow ($\dot{m}$) and temperature across, e.g., the DOC and DPF (T), i.e., SLp=f($\Delta P$, $\dot{m}$, T). Sensors 30 for measuring temperature, flow monitors 32, and the like can be provided at various points in the EATS and the engine 21 for measuring various characteristics of the exhaust, and can send signals to the controller 31. The normal models for calculating soot load based on pressure drop considers only pressure drop due to a so-called "cake layer" of soot. A so-called "deep bed soot load" in pores of the DPF, however, can substantially increase resistance to flow through a DPF and can be a source of significant error in the pressure drop soot load models.

The controller 31 is also arranged to calculate what shall be denominated as an emissions based soot load estimate SLc based on soot output calculated from an engine model. Ordinarily, the engine model will calculate soot output based on data including one or more of engine rpms, air-to-fuel ratio (AFR), EGR usage, and fuel angle (i.e., how far ahead or behind of top-deadcenter fuel injection and/or ignition occurs), temperature measurements such as ambient temperature, engine inlet temperature, engine exhaust temperature, DOC inlet temperature, and DPF inlet and outlet temperature, and NOx emissions measurements. The engine model will ordinarily also calculate soot consumption due to NO2 and O2 based soot regeneration of the DPF and use the calculated soot consumption rate to calculate the emissions based soot load estimate SLc. It will be appreciated that engine models for calculating soot load and/or consumption, and factors used in those calculations, will vary depending upon the engine and EATS in question, as well as upon the particular model used.

The controller 31 is further arranged to compare the pressure drop based soot load estimate SLp with the emissions based soot load estimate SLc. The controller 31 forms part of a warning system in that it is arranged to provide a warning, such as by lighting a dashboard light 33, if a difference between the pressure drop based soot load estimate SLp and the emissions based soot load estimate SLc exceeds a predetermined value. Exceeding the predetermined value will suggest abnormally frequent regeneration, which can be indicative of other problems, particularly excessive soot production or DOC catalyst malfunction, and can be used to trigger an alarm or indicator such as the light.

Figure 2:
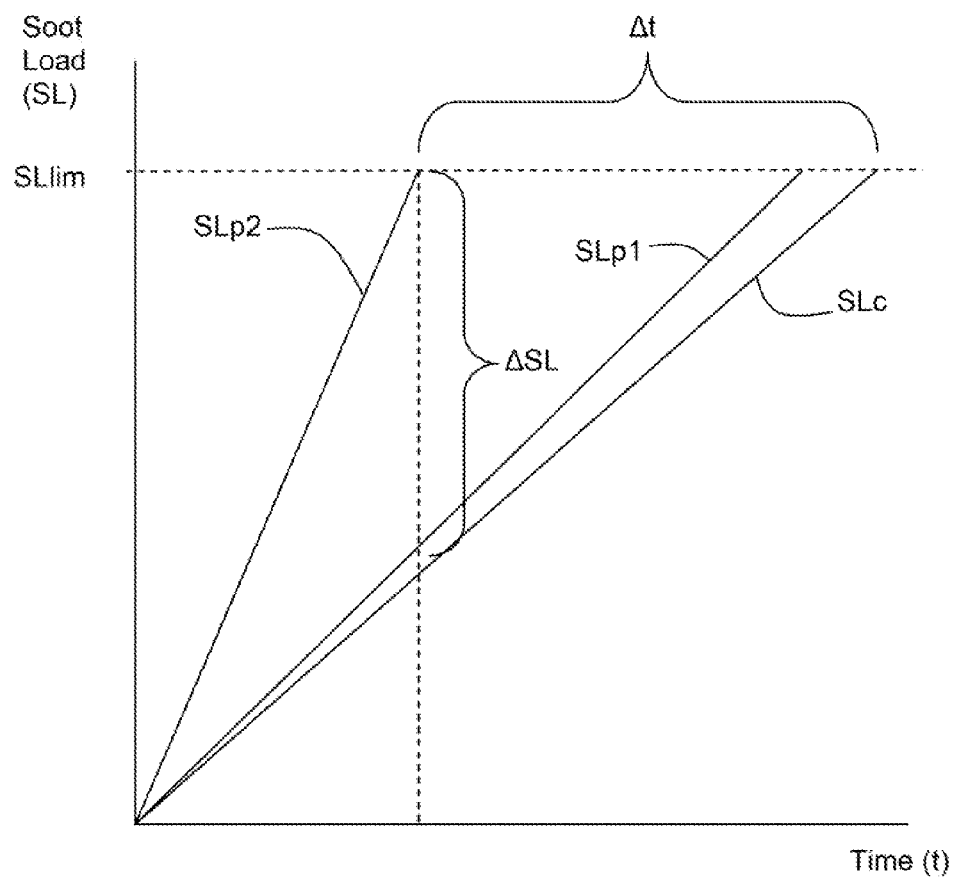
FIG. 2 is a graph illustrating how pressure based soot load estimates and emissions based soot load estimates can be used to determine abnormal regeneration frequency.

FIG. 2 graphically shows how the predetermined value can be, for example, an amount of time $\Delta t$ between the time that the pressure based soot load estimate SLp2 actually reaches the limit value SLlim and the time that it is predicted that the emissions based soot load estimate SLc will take to reach the limit value, or the difference in soot loading $\Delta SL$ estimated by the pressure based soot load estimate and the emissions based soot load estimate when the pressure based soot load estimate reaches the limit value. Other techniques for measuring an excessive deviance between the pressure based soot load estimate SLp and the emissions based soot load estimate SLc may be used instead of or in addition to differences in time or soot load. FIG. 2 graphically illustrates how, with a properly operating engine and DOC, the pressure based soot load estimate SLp1 and the emissions based soot load estimate SLc will be expected to closely follow one another over time. The graph of FIG. 2 is merely illustrative and is not intended to represent actual soot loading data estimates.

When the difference between the pressure drop based soot load estimate SLp and the emissions based soot load estimate SLc exceeds the predetermined value, an operator or technician can check the functionality of the engine 21 and the DOC 25, or automated diagnostics can be performed to determine whether the engine and the DOC are operating properly.

Usually, the controller 31 is arranged to compare the pressure drop based soot load estimate SLp with the emissions based soot load estimate SLc at least when one of the pressure drop based soot load estimate SLp and the emissions based soot load estimate SLc reaches a predetermined soot load limit SLlim, although the controller may also continuously compare the pressure drop based soot load estimate with the emissions based soot load estimate and provide a warning whenever a difference between estimated values exceeds some amount or percentage of soot loading, or some other measure for comparing the soot load estimates may be chosen. The controller 31 can be arranged to trigger a DPF regeneration, such as by injection of hydrocarbons upstream of the DPF through a so-called "seventh injector" 35, when the pressure drop based soot load estimate SLp reaches the soot load limit SLlim. It is anticipated that, when problems relating to engine soot production or DOC catalyst failure occur, the pressure based soot load estimate SLp will ordinarily reach the limit value SLlim before the emissions based soot load value SLc. Of course, a DPF regeneration can be triggered when one of the pressure drop based soot load estimate SLp and the emissions based soot load estimate SLc reaches the predetermined soot load limit SLlim.

Figure 3:
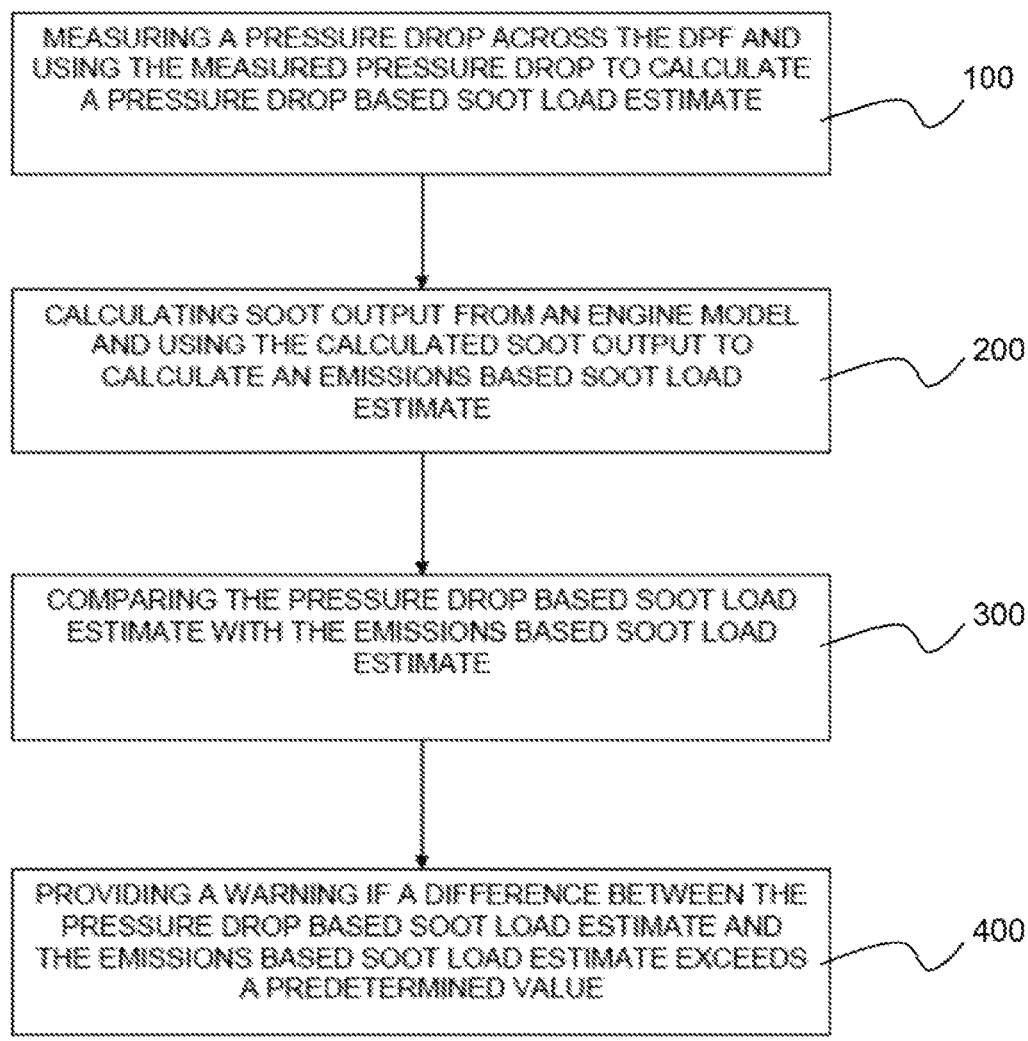
FIG. 3 is a flow chart illustrating steps in a method for determining abnormal regeneration frequency.

FIG. 3 shows steps in a method for detecting abnormally frequent DPF 27 regeneration. According to the method, at step 100, a pressure drop across the DPF 27 is measured, and the measured pressure drop is used to calculate a pressure drop based soot load estimate SLp.

At step 200, soot output from an engine model is calculated and the calculated soot output is used to calculate an emissions based soot load estimate SLc. The emissions based soot load estimate SLc will ordinarily also involve calculation of soot consumption due to NO2 and O2 based soot regeneration. Soot output and soot consumption will ordinarily be calculated based on data including engine rpms, air-to-fuel ratio (AFR), EGR usage, and fuel angle (i.e., how far ahead or behind of top-dead-center fuel injection and/or ignition occurs), temperature measurements such as ambient temperature, engine inlet temperature, and exhaust temperature, and NOx emissions measurements.

At step 300, the pressure drop based soot load estimate SLp is compared with the emissions based soot load estimate SLc. The pressure drop based soot load estimate SLp may be compared with the emissions based soot load estimate SLc when one of the pressure drop based soot load estimate and the emissions based soot load estimate reaches the limit value SLlim, at some other point, or continuously.

At step 400, a warning is provided if a difference between the pressure drop based soot load estimate SLp2 and the emissions based soot load estimate SLc exceeds a predetermined value, such as an excessive period of time $\Delta t$ between times when the pressure drop based soot load estimate SLp2 reaches a soot load limit value SLlim or an excessive amount of difference in soot loading estimates $\Delta SL$ at a time when the pressure drop based soot load estimate reaches the soot load limit value.

In the present application, the use of terms such as "including" is open-ended and is intended to have the same meaning as terms such as "comprising" and not preclude the presence of other structure, material, or acts. Similarly, though the use of terms such as "can" or "may" is intended to be open-ended and to reflect that structure, material, or acts are not necessary, the failure to use such terms is not intended to reflect that structure, material, or acts are essential. To the extent that structure, material, or acts are presently considered to be essential, they are identified as such.

While this invention has been illustrated and described in accordance with a preferred embodiment, it is recognized that variations and changes may be made therein without departing from the invention as set forth in the claims.

What is claimed is:

1. A method for diagnosing engine and exhaust aftertreatment system health by detecting abnormally frequent diesel particulate filter (DPF) regeneration, comprising:
    operating an engine and an exhaust aftertreatment system downstream of the engine, the exhaust aftertreatment system comprising a DPF;
    measuring a pressure drop across the DPF and using the measured pressure drop to calculate a pressure drop based soot load estimate;
    calculating soot output from an engine model and using the calculated soot output calculate an emissions based soot load estimate;
    comparing the pressure drop based soot load estimate with the emissions based soot load estimate when one of the pressure drop based soot load estimate and the emissions based soot load estimate reaches a predetermined soot load limit;
    triggering active DPF regeneration when one of the pressure drop based soot load estimate and the emissions based soot load estimate reaches the predetermined soot load limit; and
    identifying abnormally frequent active regeneration of the DPF if a difference between the pressure drop based soot load estimate and the emissions based soot load estimate exceeds a predetermined value,
    wherein the predetermined value is a predetermined time period, the abnormally frequent regeneration being identified if a difference in time between a time at which one of the pressure drop based soot load estimate and the emissions based soot load estimate reaches the predetermined soot load limit and a time at which the other one of the pressure drop based soot load estimate and the emissions based soot load estimate is expected to reach the predetermined soot load limit exceeds the predetermined time period.

2. The method as set forth in claim 1, comprising checking functionality of the engine and a diesel oxidation catalyst (DOC) downstream from the engine after the warning is provided.

3. The method as set forth in claim 1, comprising calculating soot output based on data including one or more of engine rpms, air-to-fuel ratio, EGR usage, and fuel angle, temperature measurements including one or lore of ambient temperature, engine inlet temperature, and exhaust temperature, and NOx emissions measurements.

4. The method as set forth in claim 1, comprising calculating the pressure drop based soot load estimate based on factors including measured exhaust mass flow and exhaust temperature.

5. The method as set forth in claim 1, comprising calculating soot consumption due to NO2 and O2 based soot regeneration and using the calculated soot consumption to calculate the emissions based soot load estimate.

6. The method as set forth in claim 5, comprising calculating soot output and soot consumption based on data including one or more of engine rpms, air-to-fuel ratio, EGR usage, and fuel angle, temperature measurements including one or more of ambient temperature, engine inlet temperature, and exhaust temperature, and NOx emissions measurements.

7. A method for diagnosing engine and exhaust aftertreatment system health by detecting abnormally frequent diesel particulate filter (DPF) regeneration, comprising:
    operating an engine and an exhaust aftertreatment system downstream of the engine, the exhaust aftertreatment system comprising a DPF;
    measuring a pressure drop across the DPF and using the measured pressure drop to calculate a pressure drop based soot load estimate;
    calculating soot output from an engine model and using the calculated soot output to calculate an emissions based soot load estimate;
    comparing the pressure drop based soot load estimate with the emissions based soot load estimate when one of the pressure drop based soot load estimate and the emissions based soot load estimate reaches a predetermined soot load limit;

triggering active DPF regeneration when one of the pressure drop based soot load estimate and the emissions based soot load estimate reaches the predetermined soot load limit; and identifying abnormally frequent active regeneration of the DPF if a difference between the pressure drop based soot load estimate and the emissions based soot load estimate exceeds a predetermined value, wherein the predetermined value is a predetermined soot load quantity, the abnormally frequent regeneration of the DPF being identified if when one of the pressure drop based soot load estimate and the emissions based soot load estimate reaches the predetermined soot load limit, a difference in estimated soot load between the pressure drop based soot load estimate and the emissions based soot load estimate exceeds the predetermined soot load quantity.

8. A method for detecting possible diesel engine malfunction or diesel oxidation catalyst (DOC) malfunction, comprising:

operating an engine and an exhaust aftertreatment system downstream of the engine, the exhaust aftertreatment system comprising a DOC and a diesel particulate filter (DPF);

measuring a pressure drop across the DPF and using the measured pressure drop to calculate a pressure drop based soot load estimate;

calculating soot output from an engine model and using the calculated soot output to calculate an emissions based soot load estimate;

comparing the pressure drop based soot load estimate with the emissions based soot load estimate when one of the pressure drop based soot load estimate and the emissions based soot load estimate reaches a predetermined soot load limit;

triggering active DPF regeneration when one of the pressure drop based soot load estimate and the emissions based soot load estimate reaches the predetermined soot load limit; and identifying malfunction of at least one of the diesel engine and the DOC if a difference between the pressure drop based soot load estimate and the emissions based soot load estimate exceeds a predetermined value, wherein the predetermined value is a predetermined time period, the malfunction being identified if a difference in time between a time at which one of the pressure drop based soot load estimate and the emissions based soot load estimate reaches the predetermined soot load limit and a time at which the other one of the pressure drop based soot load estimate and the emissions based soot load estimate is expected to reach the predetermined soot load limit exceeds the predetermined time period.

9. The method as set forth in claim 8, comprising calculating soot consumption due to NO2 and O2 based soot regeneration and using the calculated soot consumption to calculate the emissions based soot load estimate.

10. A diesel engine with an exhaust after treatment system, comprising:

the diesel engine, the diesel engine comprising an exhaust;

a diesel oxidation catalyst (DOC) downstream of the diesel engine exhaust;

a diesel particulate filter (DPF) downstream of the DOC;

sensors for measuring a pressure drop across the DPF; and a controller arranged to calculate a pressure drop based soot load estimate based on the measured pressure drop, calculate an emissions based soot load estimate based on soot output calculated from an engine model, compare the pressure drop based soot load estimate with the emissions based soot load estimate when one of the pressure drop based soot load estimate and the emissions based soot load estimate reaches a predetermined soot load limit, and trigger active DPF regeneration when one of the pressure drop based soot load estimate and the emissions based soot load estimate reaches the predetermined soot load limit, identifying abnormally frequent active regeneration of the DPF if a difference between the pressure drop based soot load estimate and the emissions based soot load estimate exceeds a predetermined value, wherein the predetermined value is a predetermined time period, the abnormally frequent regeneration of the DPF being identified if a difference in time between a time at which one of the pressure drop based soot load estimate and the emissions based soot load estimate reaches the predetermined soot load limit and a time at which the other one of the pressure drop based soot load estimate and the emissions based soot load estimate is expected to reach the predetermined soot load limit exceeds the predetermined time period.

11. The diesel engine with an exhaust after treatment system as set forth in claim 10, wherein the controller is arranged to calculate soot output based on data including or more of engine rpms, air-to-fuel ratio, EGR usage, and fuel angle, temperature measurements including one or more of ambient temperature, engine inlet temperature, and exhaust temperature, and NOx emissions measurements.

12. The diesel engine with an exhaust after treatment system as set forth in claim 10, wherein the controller is arranged to calculate the pressure drop based soot load estimate based on factors including measured exhaust mass flow and exhaust temperature.

13. The diesel engine with an exhaust after treatment system as set forth in claim 10, wherein the controller is arranged to calculate soot consumption due to NO2 and O2 based soot regeneration and use the calculated soot consumption to calculate the emissions based soot load estimate.

14. The diesel engine with an exhaust after treatment system as set forth in claim 13, wherein the controller is arranged to calculate soot output and soot consumption based on data including one or more of engine rpms, air-to-fuel ratio, EGR usage, and fuel angle, temperature measurements including one or ore of ambient temperature, engine inlet temperature, and exhaust temperature, and NOx emissions measurements.

15. A warning system for a diesel engine with an exhaust after treatment system for diagnosing engine and exhaust aftertreatment system health, the exhaust after treatment system comprising a diesel oxidation catalyst (DOC) downstream of an exhaust of the engine and a diesel particulate filter (DPF) downstream of the DOC, the warning system comprising:

sensors for measuring a pressure drop across the DPF, and a controller arranged to calculate a pressure drop based soot load estimate based on the measured pressure drop, calculate an emissions based soot load estimate based on soot output calculated from an engine model, compare the pressure drop based soot load estimate with the emissions based soot load estimate when one of the pressure drop based soot load estimate and the emissions based soot load estimate reaches a predetermined soot load limit, and identifying malfunction of at least one of the engine and the DOC if a difference between the pressure drop based soot load estimate and the emissions based soot load estimate exceeds a predetermined value, wherein the predetermined value is a predetermined time period, the malfunction being identified if a difference in time between a time at which one of the pressure drop based soot load estimate and the emissions based soot load estimate reaches the predetermined soot load limit and a time at which the other one of the pressure drop based soot load estimate and the emissions based soot load estimate is expected to reach the predetermined soot load limit exceeds the predetermined time period, and wherein the controller is arranged to trigger a DPF regeneration active DPF regeneration when one of the pressure drop based soot load estimate and the emissions based soot load estimate reaches the predetermined soot load limit.

\* \* \* \* \*